(12) United States Patent
Tanaka

(10) Patent No.: US 7,075,315 B2  
(45) Date of Patent: Jul. 11, 2006

(54) APPARATUS AND METHOD FOR NON-DESTRUCTIVE INSPECTION

(75) Inventor: Shogo Tanaka, Yamaguchi-ken (JP)

(73) Assignee: Mitsubishi Heavy Industries, Ltd., Tokyo (JP)

(*) Notice: Subject to any disclaimer, the term of this patent is extended or adjusted under 35 U.S.C. 154(b) by 0 days.

(21) Appl. No.: 10/290,322

(22) Filed: Nov. 8, 2002

(65) Prior Publication Data
US 2003/0098697 A1    May 29, 2003

(30) Foreign Application Priority Data
Nov. 12, 2001  (JP) .............. 2001-346003
May 9, 2002  (JP) .............. 2002-134489

(51) Int. Cl.
G01R 27/32    (2006.01)
G01V 3/12    (2006.01)

(52) U.S. Cl. ................... 324/642; 324/337

(58) Field of Classification Search ........ 324/637, 324/642, 644, 647, 456, 326, 535, 533, 534, 324/337
See application file for complete search history.

(56) References Cited

U.S. PATENT DOCUMENTS

| 3,836,960 | A * | 9/1974 | Gehman et al. ........... 342/27 |
| 4,896,116 | A * | 1/1990 | Nagashima et al. ...... 324/329 |
| 5,748,003 | A * | 5/1998 | Zoughi et al. ............ 324/644 |
| 5,777,891 | A * | 7/1998 | Pagano et al. ............ 702/39 |
| 6,222,373 | B1 * | 4/2001 | Morrison .................. 324/534 |
| 6,359,446 | B1 * | 3/2002 | Little, Jr. .................. 324/637 |
| 6,367,330 | B1 * | 4/2002 | Schafer ..................... 73/598 |
| 6,856,280 | B1 * | 2/2005 | Eder et al. ................ 342/147 |

* cited by examiner

Primary Examiner—Anjan Deb
(74) Attorney, Agent, or Firm—Wenderoth, Lind & Ponack, L.L.P.

(57) ABSTRACT

A non-destructive inspection apparatus includes a transmitting section, a reception section and a processing unit. The transmission section irradiates an electromagnetic wave signal toward an inspection target. The reception section receives a reflected electromagnetic wave signal from the inspection target to generate a received wave signal. The processing unit generates a fundamental reflected wave signal predicted to be received from each reflection point of the inspection target, and determines the existence or non-existence of any defects in the inspection target and the details of the defect, if it exists, based on a pattern matching between a waveform of the received wave signal and a waveform of a linear combination of fundamental reflected wave signals.

22 Claims, 6 Drawing Sheets

APPARATUS AND METHOD FOR NON-DESTRUCTIVE INSPECTION

BACKGROUND OF THE INVENTION

1. Field of the Invention

The present invention relates to a non-destructive inspection apparatus and method for inspecting a target structure.

2. Description of the Related Art

Conventionally, there are known non-destructive inspection methods of detecting a defect, such as a crack and a cavity, in a concrete structure, such as a tunnel and a bridge. As one of the non-destructive inspection methods, a so-called hammering test method is known.

In the hammering test method, the defect is detected from a reaction, a tone and the like brought about when a skilled inspector makes an impact on the concrete structure with a hammer. However, in this hammering test method, the reliability in detecting and diagnosing the defects, such as cracks and cavities, is low, and a difference in the diagnosis result between inspectors is large. Also, it is that a consecutively inspectable time is limited to about 30 minutes. Thus, the hammering test method is an inspection method whose load on the inspector is extremely heavy.

By the way, there are social backgrounds of rapid increase in the number of diagnosis targets from the viewpoint that concrete structures are desired to be used for a long time, and in the rapid decrease of the number of inspectors in recent years. For these reasons, new diagnosis methods have been demanded to be developed in which even a non-skilled inspector can carry out the diagnosis with a high accuracy. From this viewpoint, the development of various inspection methods, such as an infrared ray method, an X-ray method, an ultrasonic method, an electromagnetic wave method, have been tried instead of the hammering test method.

In the infrared ray method, the diagnosis is carried out based on a temperature difference between the front and periphery of the crack in the concrete structure. However, the detection of the crack is difficult in the case of an inspection target with no sunshine, such as inside a tunnel. For this reason, the method is available in tunnels only when the surface of the inspection target is heated, for example, with a halogen lamp. In addition, the method takes a long time for inspection and only a crack existing in a place less than 5 mm deep from the surface can be detected.

In the X-ray method, the treatment of the apparatus used in the inspection is not only troublesome, but also only a qualified person can carry out the inspection. In addition, a risk is involved and a cost of the inspection becomes expensive. Furthermore, the method cannot be applied to a structure, such as a tunnel, where the diagnosis must be carried out only from one side.

The ultrasonic method is a method which determines the existence or non-existence of a detect in a concrete structure by detecting the reflected wave from the defect and determines the position of the defect in accordance with a propagation time when an ultrasonic wave is irradiated to an inspection target. Typically, in the ultrasonic method, the first reflected wave from the defect is detected to measure the round propagation time from the concrete surface to the defect. However, it is difficult to detect the first reflected wave, and consequently to measure the round propagation time, since a composite wave of strongly superposed multi-reflected waves is observed by the ultrasonic sensor. For this reason, the ultrasonic diagnosis method of the concrete structure is proposed based on a multiple reflected wave motel or a standing wave model. However, in the ultrasonic diagnosis of the concrete structure based on the multiple reflected wave model or the standing wave model, an ultrasonic sensor needs to be in contact with the surface of the concrete structure. Consequently, it takes an extremely long time to carry out the inspection for a tunnel or the like, although there is no problem in its use for a case where an inspection target is small.

From the viewpoints of reducing an inspection time and improving a working efficiency of the inspection, an inspection method using an electromagnetic wave was proposed where a vehicle with an electromagnetic radar runs within a tunnel and achieves the inspection.

However, in the conventional inspection using the electromagnetic radar, diagnosis is carried out by converting the received electromagnetic wave signal into a picture of time-space intensity distribution. Thus, an excellent result is hardly obtained.

SUMMARY OF THE INVENTION

Therefore, an object of the present invention is to provide a non-destructive inspection apparatus and method which uses an electromagnetic wave and carries out the inspection of defects in a target structure in a short time with a high accuracy and a high reliability.

In an aspect of the present invention, a non-destructive inspection apparatus includes a transmission section, a reception section and a processing unit. The transmission section irradiates an electromagnetic wave signal toward an inspection target. The reception section receives a reflected electromagnetic wave signal from the inspection target to generate a received wave signal. The processing unit generates a fundamental reflected wave signal predicted to be received from each of reflection points of the inspection target, and determines existence or nonexistence of any defects in the inspection target based on a waveform of the received wave signal and a waveform of the fundamental wave signal.

Here, the processing unit may carry out a pattern matching between the waveform of the received wave signal and the waveform of the fundamental wave signal and determines the existence or nonexistence of any defects in the inspection target based on the pattern matching result. In this case, the processing unit may generate predicted wave signals assumed under defect hypotheses, each of the predicted wave signals being a linear combination of the fundamental wave signals with different round propagation times relating to the defects as variables.

Also, the processing unit may include a waveform synthesizing section and a pattern matching section. The waveform synthesizing section generates predicted wave signals assumed under defect hypotheses in which defects are different in number and types, when its determined that the defects exist in the inspection target. The pattern matching section carries out a pattern matching between the waveform of the received wave signal and a waveform of each of the predicted wave signals to determine the least matching angle under each of the defect hypotheses, determines a minimum matching angle from among the least matching angles for the defect hypotheses, and determines one of the defect hypotheses realizing the minimum matching angle. In this case, the defect hypotheses are a case of one crack, a case of two cracks, a case of one cavity, and a case of one crack and one cavity.

Also, the pattern matching section may determine the number of defects, a type of each of the defects, and a position of each of the defects based on the predicted wave signal calculated for the determined defect hypothesis.

Also, each of the predicted wave signals may be represented as a linear combination of the fundamental wave signals with different round propagation times relating to the defects as variables. In this case, linear combination coefficients of the linear combination are preferably determined based on each of the defect hypotheses. The pattern matching section may determine the least matching angle between the waveform of the received wave signal and the waveform of a corresponding one of the predicted wave signals for every defect hypothesis while varying the round propagation times. Also, the pattern matching section may determine an optimal approximation error when the received wave signal is orthogonally projected to a space spanned by the fundamental wave signals corresponding to each of the defect hypotheses under a constraint of a sign on each of the linear combination coefficients while varying round propagation times of the fundamental wave signals, end determine the least matching angle for each defect hypothesis based on the optimal approximation error and the received wave signal.

Also, the pattern matching section may determine the optimal predicted wave signal when the difference between the received wave signal and the predicted wave signal from the fundamental wave signals corresponding to each of the defect hypotheses is minimized, varying the round propagation times of the fundamental wave signals, and determine the least matching angle for each defect hypothesis based on the optimal predicted wave signal and the received wave signal.

Also, the pattern matching section may introduce a weight on at least one part of the waveform of the received wave signal to decrease the effect from the received wave signal from a surface of the inspection target.

Also, the pattern matching section clay generate derivatives of the received wave signal and each of the predicted wave signals and carry out the pattern matching between the derivatives corresponding to the received wave signal and each of the predicted wave signals.

In another aspect of the present invention, a non-destructive inspection method is achieved by (a) irradiating an electromagnetic wave signal toward an inspection target; by (b) receiving a reflected electromagnetic wave signal from the inspection target to generate a received wave signal; by (c) providing a fundamental wave signal predicted to be received from each of reflection points of the inspection target; by (d) determining existence or nonexistence of any defects in the inspection target based on a waveform of the received wave signal and a waveform of the fundamental wave signal; by (e) generating predicted wave signals which are different from each other under defect hypotheses; and by (f) determining the number of the defects, a type of each of the defects, and a position of each of the defects in the inspection target based on the waveform of the received wave signal and a waveform of each of the predicted wave signals.

Here, the defect hypotheses may be a case of one crack, a case of two cracks, a case of one cavity, and a case of one crack and one cavity.

Also, each of the predicted wave signals may be a linear combination of the fundamental wave signals with round propagation times relating to the defects as variables.

Also, the (d) determining step may be achieved by carrying out a pattern matching between the waveform of the received wave signal and the waveform of the fundamental wave signal; and by determining the existence or nonexistence of any defects in the inspection target based on the pattern matching result.

Also, the (f) determining step may be achieved by (g) determining the least matching angle for each of the defect hypotheses based on the waveform of the received wave signal and the waveform of a corresponding one of the predicted wave signals. In this case, the (g) determining step may be achieved by carrying out a pattern matching between the waveform of the received wave signal and the waveform of each of t the predicted wave signals to determine the least matching angle for a corresponding one of the defect hypotheses.

Also, the (f) determining step may further include: determining a minimum matching angle from among the least matching angles for the defect hypotheses; and determining one of the defect hypotheses corresponding to the minimum matching angle. In this case, the (f) determining step may further include determining the number of the defects and a type of each of the defects based on the determined defect hypothesis; and determining a position of each of the defects based on round propagation times relating to the determined defect hypothesis.

Also, the (f) determining step may be achieved by determining an optimal approximation error when the received wave signal is orthogonally projected to a space spanned by the fundamental wave signals defined by each of the defect hypotheses under constraint of sign of each of the linear combination coefficients while varying round propagation times of the fundamental wave signals; and by determining the least matching angle for each hypothesis based on the optimal approximation error and the received wave signal.

Also, the (f) determining step may be achieved by determining an optimal predicted wave signal when a difference between the received wave signal and a corresponding one of the predicted wave signals from the fundamental wave signals corresponding to each of the defect hypotheses is minimized, varying the round propagation times of the fundamental wave signals; and by determining the least matching angle for each defect hypothesis based on the optimal predicted wave signal and the received wave signal.

If there is a non-concrete body, such as a steel skeleton, a reinforcing bar, a foreign substance, a crack, a cavity and the like, inside the target concrete structure, the electromagnetic wave irradiated to the concrete structure is reflected by the non-concrete body, and is received by the receiving antenna. Then, a pattern matching is carried out between the actual received wave signal received by the receiving antenna and the predicted wave signal generated under each defect hypothesis that some non-concrete bodies exist in various states inside the concrete structure. Thus, one of the predicted wave signals having the best pattern matching to the actual received wave signal is determined, and the situation of the non-concrete bodies inside the concrete structure can be diagnosed.

In the non-destructive inspection method of the concrete structure, the waveform of the predicted wave signal can be represented as a linear combination of waveforms of fundamental reflected waves reflected by the one or more non-concrete bodies inside the concrete structure.

If the one or more non-concrete bodies exist inside the concrete structure, the irradiated electromagnetic wave is respectively reflected by the respective non-concrete bodies. The electromagnetic wave thus reflected once by one of the non-concrete bodies may be repeatedly reflected by the other parts during the propagation in the concrete structure, resulting in the large attenuation of the electromagnetic wave.

Thus, as compared with the electromagnetic wave reflected once by each non-concrete body and detected by the receiving antenna, the strength of the electromagnetic wave detected by the receiving antenna after two or more reflections is small. Therefore, if the fundamental reflected wave is preliminarily defined, the waveform of the predicted wave signal from the concrete structure in which one or more non-concrete bodies exist can be generated through a linear combination of the waveforms of the fundamental reflected waves reflected once by the respective non-concrete bodies. Hence, if the pattern matching is carried out between the waveform of the predicted wave signal and waveform of the actual received wave signal, identification of each non-concrete body and their positions can be determined based on thus-calculated round propagation times of the predicted wave signal and the selected defect hypothesis.

In the non-destructive inspection method of the concrete structure, the minimum matching angle is used for evaluating the level of the pattern matching, and is calculated using the received wave signal and its orthogonally projected wave signal to a space spanned by several fundamental reflected waves (with a constraint on the sign of the linear combination coefficients) varying the round propagation times for each defect hypothesis. The position of the non-concrete bodies and their kind can be determined based on the defect hypothesis and round propagation times which give the minimum matching angle.

In order to carry out the optimal pattern matching between the waveform of the actual received wave signal and the waveform of the predicted wave signal represented as a linear combination of the fundamental reflected wave signals, it is necessary to optimize the linear combination coefficients and the round propagation times of the respective fundamental reflected waves. However, if the pattern matching is carried out with all the linear combination coefficients and the round propagation times as variables for the optimization, this is not practical since there is a risk of falling in a local minimum around a true one and a vast time is required for the optimization. For these reasons, the linear combination coefficients are analytically determined, whereas the round propagation times of the fundamental reflected waves are determined numerically by shifting the times. Thus, the local minimum is avoided and the computation time is extremely reduced.

That is, if the kind of the defect is assumed, and the predicted wave signal is generated by letting the positions be variables (i.e., by letting the round propagation times of the fundamental reflected waves be the variables), then, the linear combination coefficients for the optimal pattern matching are analytically solved for the given round propagation times. The optimal matching angle is used as the measure for evaluating the similarity between the waveforms of the optimal predicted wave signal and the actual received wave signal under each hypothesis and the round propagation times. Here, the optimal matching angle is the function of the round propagation times indicative of the positions of the non-concrete bodies. Thus, when the positions of the non-concrete bodies, i.e., the round propagation times are varied such that the optimal matching angle is minimum, the optimal pattern matching of the waveform of the predicted wave signal to the actual received wave signal is completed for each detect hypothesis. Finally, when a defect hypothesis is selected which minimizes the optimal matching angle among the given defect hypotheses, the final optimal pattern matching is completed between the waveform of the received wave signal and the waveform of the predicted wave signal under the given defect hypotheses. At this time, the round propagation times are the variables to be sought in the non-destruction inspection to obtain the least matching angle for each defect hypothesis.

DESCRIPTION OF THE PREFERRED EMBODIMENTS

Hereinafter, a non-destructive inspection apparatus of the present invention will be described below in detail with reference to the attached drawings. In the following description, a concrete structure is exemplified as an inspection target. However, it could be understood to a person skilled in the art that the inspection target is not limited to the concrete structure.

Figure 1:
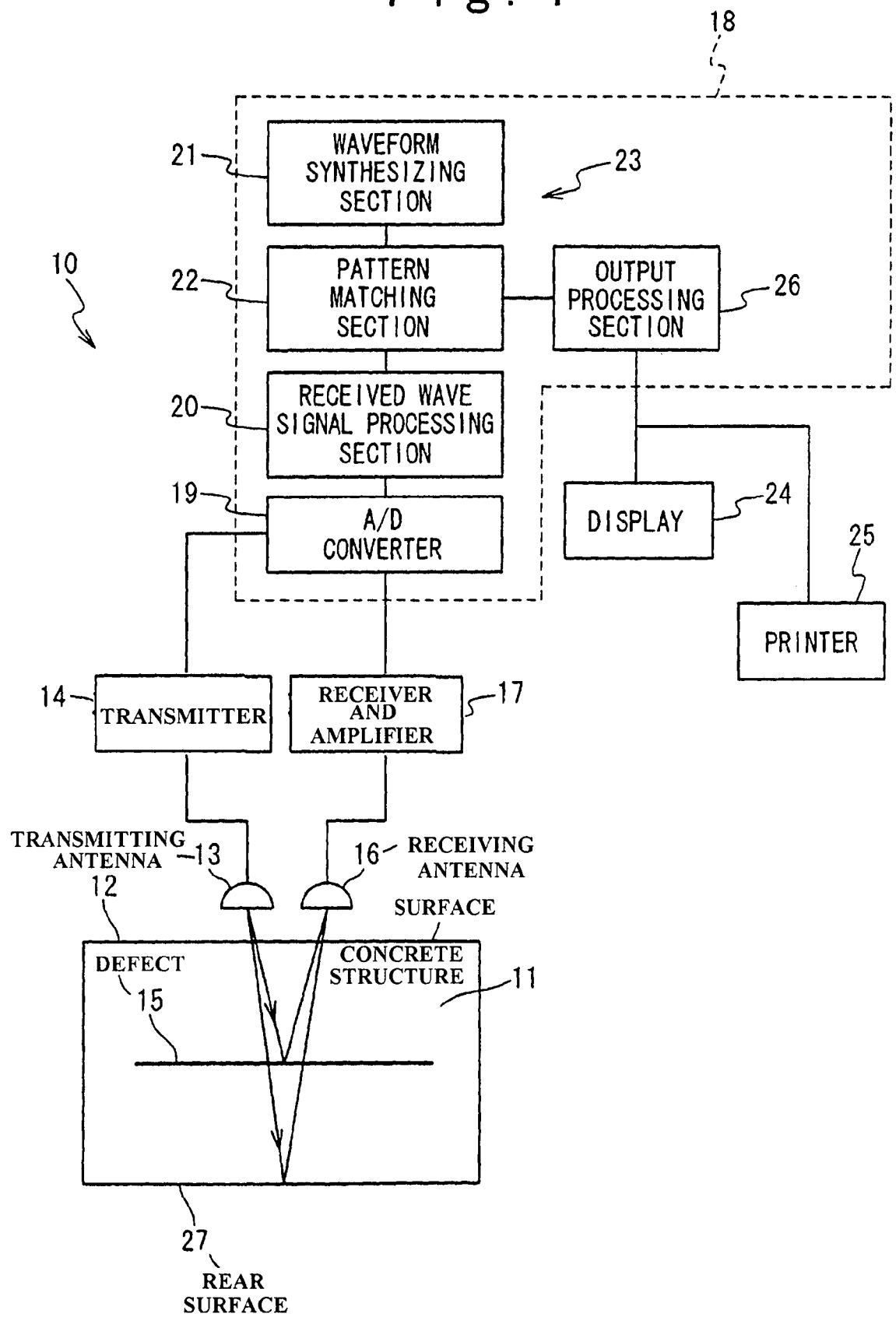
FIG. 1 is a block diagram showing a non-destructive inspection apparatus according to the present invention.

FIG. 1 is a block diagram showing the non-destructive inspection apparatus according to the present invention. Referring to FIG. 1, the non-destructive inspection apparatus 10 of the present invention is composed of a transmitting antenna 13, a transmitter 14, a receiving antenna 16, and a receiver and amplifier 17. The transmitting antenna 13 is faced to the surface 12 of a concrete structure 11, and the transmitter 14 transmits an electromagnetic wave signal to the concrete structure 11. The receiving antenna 16 is faced to the surface 12 of the concrete structure 11, and receives reflected electromagnetic wave signals from the concrete structure surface 12 and a defect 15 as an example of a non-concrete structure existing inside the concrete structure 11. The receiver and amplifier 17 amplifies the received signal by the receiving antenna 16. The units having known structures may be preferably used as the transmitter 14 and the receiver and amplifier 17.

The electromagnetic wave having a frequency of an order of several hundreds MHz to several GHz can be used for the non-destructive inspection of the concrete structure 11. However, the electromagnetic wave signal of any frequency may be used in principle. The frequency of the electromagnetic wave may be varied based on the inspection target or the depth of the defect 15 to be detected even in a case of the same target.

The non-destructive inspection apparatus 10 of the present invention is further composed of a processing unit 18, a display 24 and a printer 25. The processing unit 18 processes the received reflected wave signal amplified by the amplifier 17. The processing unit 18 is composed of an A/D converting section 19, a received wave signal processing section 20, a waveform synthesizing section 21, a pattern matching section 22, and an output processing section 26. The waveform synthesizing section 21 and the pattern matching section 22 constitute a waveform processing section 23. The A/D converting section 19 carries out A/D conversion on the received wave signal from the amplifier 17. The received wave signal processing section 20 generates the waveform R(t) of the received wave signal from the output of the A/D converting section 19. The waveform synthesizing section 21 synthesizes the waveforms r(t) of predicted wave signals predicted from the defect 15 existing in the concrete structure 11. The pattern matching section 22 carries out a pattern matching between the waveform r(t) of each of the predicted wave signals and the waveform R(t) of the received wave signal. The output processing section 26 outputs the pattern matching result and the defect diagnosis result to the display 24 or the printer 25.

It should be noted that the processing unit 18, the display 24 and the printer 25 may be a part of a computer. The non-destructive inspection method may be achieved based on a program loaded on the processing unit 18.

Next, the operation of the non-destructive inspection apparatus according to the present invention will be described below.

The transmitting antenna 13 transmits an electromagnetic wave signal towards the concrete structure 11. The electromagnetic wave is reflected from the concrete structure 11 and is immediately detected by the receiving antenna 16. The reflected wave signal received by the receiving antenna 16 is amplified by the amplifier 17, and sent through the A/D converting section 19 to the received wave signal processing section 20, which generates the waveform R(t) of the received wave signal. Then, the waveform R(t) of the received wave signal is sent to the pattern matching section 22.

At first, some kinds of defects such as a crack and a cavity, which are assumed to be inside the concrete structure 11, are inputted as the number of defects and the combination pattern of the defects to the waveform synthesizing section 21 of the waveform processing section 23. The round propagation times corresponding to the depths of the defects are also inputted.

The waveform synthesizing section 21 generates the waveform r(t) of a predicted wave signal predicted to be reflected from a concrete structure as the inspection target, based on the following propagation model in accordance with the inputted data. For example, it is supposed that one defect 15 exists inside the concrete structure 11, as shown in FIG. 1. If the electromagnetic wave signal is assumed to be irradiated from the transmitting antenna 13 vertically to the surface 12 of the concrete structure 11, the electromagnetic wave signal is firstly reflected by the front surface 12 of the concrete structure 11, and then the reflected wave signal is received by the receiving antenna 16. In actuality, a part of the irradiated electromagnetic wave transmits through the front surface 12 of the concrete structure 11 and propagates through the concrete structure until it is reflected by the defect 15 existing inside the concrete structure 11. The reflected wave signal transmits through the surface 12 of the concrete structure 11 and is received by the receiving antenna 16. Moreover, another part of the electromagnetic wave signal propagates through the defect 15, is reflected by a rear surface 27 of the concrete structure 11, propagates back through the defect 15 and the surface 12 of the concrete structure 11, and finally is received by the receiving antenna 16. In this case, the intensity (amplitude) of the electromagnetic wave signal propagating through the concrete structure 11 is attenuated based on a propagation distance corresponding to the round propagation time. Thus, the amplitude of the electromagnetic wave signal reflected near the front surface 12 is large as compared with that of the electromagnetic wave signal reflected by the rear surface 27.

As mentioned above, the transmission and reception of the electromagnetic wave signal have been described by exemplifying the case where the single defect 15 exists inside the concrete structure 11. If the defect 15 inside the concrete structure 11 is a cavity, the electromagnetic wave signal is reflected by the front surface and rear surface of the cavity, and the reflected wave signals are received by the receiving antenna 16 at different times corresponding to the round propagation times depending on the reflection points. In this case, the amplitude of the received reflected wave signal is different depending on the length of a propagation path and a type of the defect. However, the waveforms of the reflected wave signals from different reflection points are substantially similar to each other, although the amplitudes are different.

From this viewpoint, the reflected wave signal having the substantially similar waveform is referred to as a fundamental reflected wave signal hereinafter, and the waveform of the fundamental reflected wave signal is represented by $r_0(t)$. Here, it is supposed that a plurality of defects 15 exist just under the transmitting and receiving antennas 13 and 16. The respective reflected wave signals from the respective defects 15 are sequentially received by the receiving antenna 16 after the round propagation times corresponding to the positions of the respective defects 15. Thus, the waveform r(t) of the predicted wave signal predicted to be received by the receiving antenna 16 can be represented as follows, as a linear combination of the waveforms of the fundamental reflected waves whose round propagation times are different:

$$r(t)=c_1 r_0(t-T_1)+c_2 r_0(t-T_2)+c_3 r_0(t-T_3)+ \qquad (1)$$

where the linear combination coefficients $c_1, c_2, \ldots$ are calculated theoretically. The time $T_1$ is a round propagation time of the first electromagnetic wave from the front surface 12 of the concrete structure 11, that is, the time from the time when the electromagnetic wave signal is irradiated from the transmitting antenna 13 to the time when the electromagnetic wave signal from the front surface 12 of the concrete structure 11 is received by the receiving antenna 16. Also, the times $T_2$ and $T_3$ are round propagation times until the first electromagnetic wave signals from the respective defects 15 arrive at the receiving antenna 16.

The second or higher-order reflected waves can be neglected for their many reflections and large attenuation inside the concrete structure 11. Hence, the waveform r(t) of the predicted wave signal can be represented by a linear combination of only the waveforms of the first reflected waves from the front surface 12 of the concrete structure 11 and the defects 15 inside the concrete structure 11.

As understood from the above, a representative reflected wave signal received by the receiving antenna 16 is predetermined theoretically. The waveform synthesizing section 21 generates a fundamental reflected wave signal theoretically or experimentally, and generates the waveform r(t) of a predicted wave signal as a linear combination of the fundamental reflected wave signals $r_0(t)$ with the round propagation times shifted to each other. In order to determine the fundamental reflected waveform $r_0(t)$ experimentally, a concrete block with the thickness of about 500 mm and with no defects therein is prepared. An electromagnetic wave signal is irradiated to it. The reflected wave signal is received and memorized as the waveform $r_0(t)$ of the fundamental reflected wave signal. Since the concrete structure contains no defects therein, the received reflected wave signal is regarded as the reflected wave signal only from the concrete structure surface. The fundamental reflected wave signal may be determined from the experiment, or may be estimated from the electromagnetic radar characteristics of the concrete structure theoretically.

Generally, one of the purposes to carry out the non-destructive inspection of the concrete structure 11 is to detect the defect 15, such as a crack or a cavity, which exists inside the concrete structure 11. In such a case, the waveform of the received reflected wave signal and that of the predicted wave signal are compared, and whether the defect exists in the concrete structure is determined. For, the comparison, a pattern matching is effective and here carried out. When the pattern matching is carried out for the non-destructive inspection, it is enough to consider the following five cases about the existence of defects in the depth direction of the concrete structure 11 (i.e., defect hypotheses): (1) a case of no defect, (2) a case of one crack, (3) a case of two cracks, (4) a case of one cavity, and (5) a case of one crack and one cavity. In this way, it is not necessarily needed to carry out the general pattern matching using the equation (1). Instead, an optimal pattern matching is carried out between the received wave signal R(t) and each of the predicted wave signals r(t) generated under the assumptions of the above mentioned five cases.

Consequently, the waveform synthesizing section 21 defines a predicted wave signal r(t) predicted to be received by the receiving antenna 16 by using several fundamental reflected waveforms $r_0(t)$ whose round propagation times $T_1, T_2, \ldots$ are variables in accordance with each defect hypothesis. In this case, the linear combination coefficients for the above five cases are calculated theoretically using the round propagation times, transmittances and reflectances, and an attenuation rate in the concrete structure 11.

When it is supposed that the optimal pattern matching is performed on the above five defect hypotheses for the concrete structure 11, it is necessary to optimize the linear combination coefficients $c_1, c_2, c_3, \ldots$ and the round propagation times $T_1, T_2, T_3, \ldots$ of the equation (1) for each hypothesis. If the optimization is carried out by assuming all of the linear combination coefficients and the round propagation times as variables, this is not in practical use, since a vast amount of time is required for the calculation in addition to the risk of falling into a local minimum. For the reasons, analytical optimization is carried out on the linear combination coefficients $c_1, c_2, C_3, \ldots$, whereas numerical optimization is carried out only on the round propagation times $T_1, T_2, T_3, \ldots$. Here, in the numerical optimization, the round propagation times are varied and searched for such that the matching angle is the least.

Figure 3:
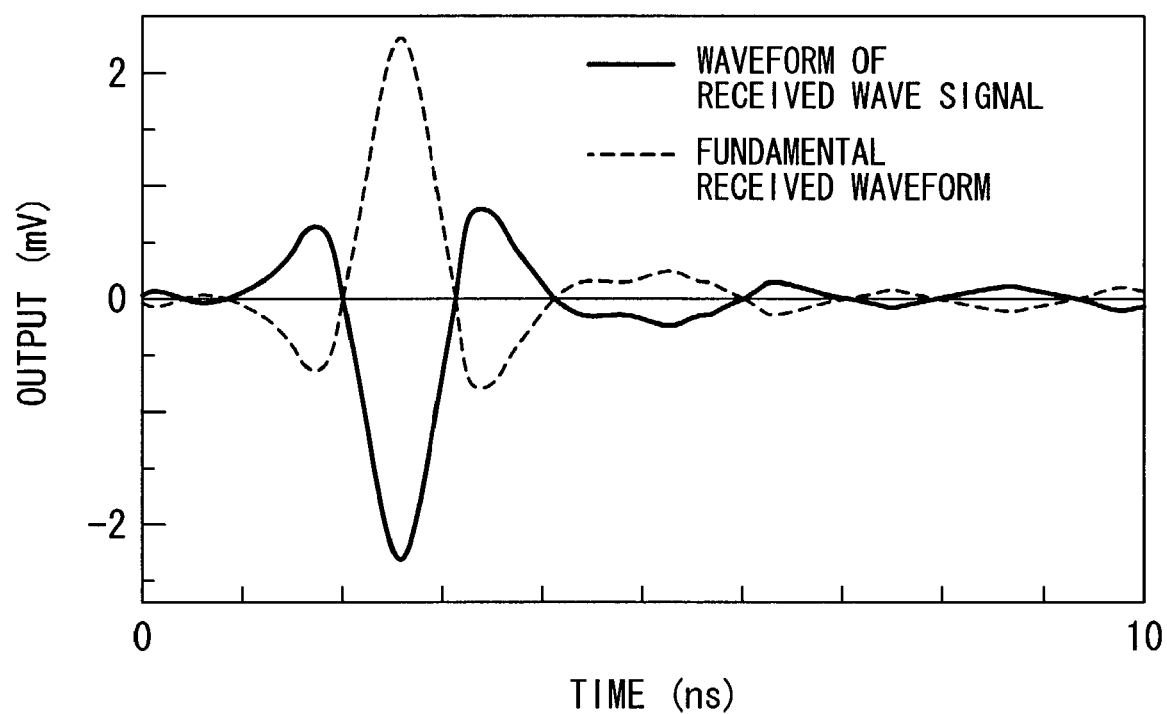
FIG. 3 is a diagram showing a fundamental reflected wave from a concrete surface.

The optimization of the linear combination coefficients $c_1$, $c_2, c_3, \ldots$ will be considered below. The transmittance of the electromagnetic wave at a boundary between different media is always positive. As for a reflectance, however, a positive or negative sign can be taken depending on the relative relation between the two media. That is, the reflectance is positive in a case of the propagation from the concrete structure to air, and the reflectance is negative in a case of the propagation from air to the concrete structure. Thus, the reflectance at the front surface 12 of the concrete structure 11 is negative, as shown in FIG. 3. On the other hand, if the defect 15 inside the concrete structure 11 is a crack, it is necessary to consider the reflection from a crack surface on the side of the front surface 12 and the reflection from a rear surface of the crack. Here, if the thickness of the crack is very thin, the difference between the front surface and rear surface of the crack in the round propagation time can be substantially ignored. Considering the contribution to a transmittance and a reflectance, the reflectance at the front surface of the crack on the side of the front surface 12 is 0.48, whereas the reflectance at the rear surface is about −0.37, i.e., −(transmittance of 0.52 from the concrete to the air)×(reflectance 0.48 at the rear surf ace)×(transmittance 1.48 from the air to the concrete)=−0.369. Thus, the reflectance as to the entire crack is 0.48−0.37=0.11. Hence, when the thickness of the crack is very thin, the reflection by the crack can be regarded as only reflection at the front surface of the crack. In this way, in the waveform r(t) of the predicted wave signal, each of the linear combination coefficients can be determined from a multiplication of a reflectance at a reflection point and the transmittances at the boundaries on the propagation path of the electromagnetic wave. If the attenuation of the electromagnetic wave through the concrete structure is considered, the multiplication may be multiplied by an attenuation rate corresponding to the round propagation time.

Through the above consideration, the linear combination coefficients $c_1, c_2, \ldots$ are functions of the round propagation times $T_1, T_2, \ldots$ as variables, as well as the waveform r(t) of the predicted wave signal does, and the number of the variables is limited based on each of the above defect hypotheses.

Next, the pattern matching process by the pattern matching section 22 will be described below.

The waveform R(t) of the received wave signal generated by the received wave signal processing section 20 is compared with that of the fundamental reflected wave signal $r_0(t)$ For the comparison, the pattern matching may be carried out with the round propagation time $T_1$ varied and the least matching angle at that time may be compared with a threshold. When the least matching angle is equal to or smaller than the threshold, it can be determined that no defect exists inside the concrete structure 11.

On the other hand, when the waveform R(t) of the received wave signal is considerably different from that of the fundamental reflected wave signal $r_0(t)$ even if the round propagation time $T_1$ is adjusted, that is, when the least matching angle is larger than the threshold, it can be determined that any defect exists inside the concrete structure 11. When a defect is determined to exist inside the concrete structure 11, the pattern matching is next carried out between the waveform R(t) of the received wave signal and the waveform r(t) of each of the predicted wave signals to identify the details of the defect 15 (for example, the type of the defect and the position and the number).

In the pattern matching, for each defect hypothesis, the round propagation times $T_1, T_2, T_3, \ldots$ are first assigned and then the linear combination coefficients $c_1, c_2, \ldots$ are analytically calculated using the transmittances and the reflectances and also the attenuation rate, as described above. Thus, the pattern matching section 22 calculates a matching angle as a function of the round propagation times relating to the defects for each hypothesis. Then, the pattern matching section 22 searches for the least matching angle for each defect hypothesis while varying the round propagation times $T_1, T_2, T_3, \ldots$. In this way, the optimal round propagation times and the least matching angle are determined for every defect hypothesis. Subsequently, the pattern matching section 22 obtains the optimal predicted wave signal with the minimum matching angle among the least matching angles.

As the result of the pattern matching, if the pattern matching is carried out between the waveform r(t) of the predicted wave signal and the waveform R(t) of the received wave signal, it is possible to determine the existence or non-existence of defects and, if being judged that any defect exists inside the concrete structure, to determine the kinds, positions and sizes of the defects 15, based on the defect hypothesis and round propagation times of $T_1, T_2, T_3, \ldots$, which realize the minimum matching angle.

Next, the transmission and reception of the electromagnetic wave signal will be described. It should be noted that the above reflectance and transmittance are treated in the case where the electromagnetic wave signal is vertically irradiated to the front surface 12 and the defect 15 of the concrete structure 11. The case where the electromagnetic wave is irradiated to them at an angle needs to be treated as follows. That is, when the electromagnetic wave signal is irradiated from a medium 1 having a dielectric constant $\in_1$ and a magnetic permeability $\mu_1$ to a medium 2 having a dielectric constant $\in_2$ and a magnetic permeability $\mu_2$ at an incident angle $\theta_i$, a part of the electromagnetic wave is reflected by a boundary surface between the media 1 and 2 at the same angle $\theta_r = \theta_i$. A reflectance $r_{ref}$ at this point is represented by the following equation (2). Here, $Z_{1=(\in_1/\mu_1)^{1/2}}$ and $Z_{2=(\in_2/\mu_2)^{1/2}}$ and $\theta_t$ is an angle of refraction.

$$r_{ref} = (Z_1 \cos \theta_i - Z_2 \cos 74_i)/(Z_1 \cos \theta_i + Z_2 \cos 74_i) \quad (2)$$

It should be noted that Snell's law represented by the following equation (3) is true $$\frac{\sin \theta_i}{\sin \theta_t} = \frac{\sqrt{\varepsilon_1/\mu_1}}{\sqrt{\varepsilon_2/\mu_2}} \quad (3)$$

On the other hand, a transmittance $\tau$ is given by the following equation (4).

$$\tau = 2Z \downarrow_t / (Z_1 \cos \theta_i + Z_2 \cos \theta_i) \quad (4)$$

In most media other than a ferromagnetic body, $\mu_1 = \mu_2$ is met. Thus, the equations (2) and (4) are simplified as the following equations (5) and (6). Here, the case where the incident angle $\theta_i$ and the angle of refraction $\theta_t$ are assumed to be zero is a case that the electromagnetic wave is vertically irradiated into the defect 15 and the front surface 12 of the concrete structure 11.

$$r = \frac{\sqrt{\varepsilon_1} \cos \theta_i - \sqrt{\varepsilon_2} \cos \theta_t}{\sqrt{\varepsilon_1} \cos \theta_i + \sqrt{\varepsilon_2} \cos \theta_t} \quad (5)$$

$$r = \frac{2\sqrt{\varepsilon_2} \cos \theta_t}{\sqrt{\varepsilon_1} \cos \theta_i + \sqrt{\varepsilon_2} \cos \theta_t} \quad (6)$$

Next, the actual detection and diagnosis will be described. A strict method and a simple method are in the pattern matching process for the diagnosis. First, the strict method will be described and the simple method will be described later.

When the optimal pattern matching is carried out under each hypothesis, the linear combination coefficients are constrained in accordance with the defect hypothesis. This is led from the following description. Once one defect hypothesis is given, the first reflected wave signal from each reflection point passes through different media. Therefore, as described above, the linear combination coefficient can be represented as a multiplication of some transmittances, one reflectance and an attenuation rate in the concrete structure. It should be noted that the attenuation in the air is neglected. The attenuation in the concrete structure is calculated using the attenuation rate $\gamma$ (dB/m). As a result, by giving a hypothesis and the round propagation times under the hypothesis, the linear combination coefficients of the above equation (1) are theoretically determined as a function of a relative dielectric constant $\in$ as a physical parameter of the concrete and an attenuation rate $\gamma$.

The crack in modeling of the received wave signal is manipulated as follows. In case of the crack, there is a thin gap between first and second concrete parts. Therefore, strictly, the wave is reflected at the boundary (front surface of the crack) between the first concrete part and air and the wave which passes through the air gap is reflected at the boundary (rear surface of the crack) between the second concrete part and the air. However, since the air gap is thin, the difference in the round propagation time can be neglected. Thus, there is no problem even if it is assumed that the reflected wave signals from the front and rear surfaces are received at the same time. The influences of the front surface and the rear surface are reflected on the linear combination coefficients.

As described above, if the round propagation times $T_1, T_2, T_3, \ldots$ are given under a defect hypothesis, the linear combination coefficients, of the first reflected wave signals from the respective reflection points can be determined uniquely from the relative dielectric constant $\in$ of the concrete and the attenuation rate $\gamma$ in the concrete structure. The round propagation times $T_1, T_2, T_3, \ldots$ in addition to the relative dielectric constant $\in$ and the attenuation rate $\gamma$ are determined for every hypothesis such that the optimal pattern matching can be carried out between the waveform $r(t)$ of the predicted wave signal obtained in this way and the waveform $R(t)$ of the actual received wave signal. In this case, the following equation (7) representing a geometric angle $\theta$ between the two waveforms is used as an evaluation function to evaluate the degree of the pattern matching.

$$\theta = \cos^{-1}\left[\frac{(R, r)}{\|R\| \cdot \|r\|}\right] \quad (7)$$

where (,) and $\|.\|$ represent inner product and norm in a Hilbert space, respectively. In the actual calculation, they are approximated by those in Euclidean space using sampling data. The defect hypothesis corresponding to the minimum matching angle determined from among the least matching angles for the respective defect hypotheses is employed as the situation of the concrete structure. At that time, the depths of the defects are determined based on the round propagation times $T_1, T_2, T_3, \ldots$, and the thickness of the cavity can be also determined.

Therefore, in the strict method, when the waveform $r_0(t)$ of the fundamental reflected wave signal is theoretically or experimentally determined, the waveform $r(t)$ of the predicted wave signal is first composed of only the first term of $r_0(t-T_1)$. In this case, a pattern matching is carried out between the waveform $R(t)$ of the received wave signal and the waveform $r(t)$ of the predicted wave signal with the round propagation time T1 varied. When the pattern matching result indicates a small matching angle, the matching is determined to be good. This fact means that the reflected wave signal is only from the concrete surface and there is no defect in the concrete structure. When the pattern matching result indicates a large matching angle, the matching is determined not to be good, and it is judged that a defect exists in the concrete structure, and a new term of the second term $r_0(t-T_2)$ is added to the waveform $r(t)$ of the predicted wave signal. Then, the pattern matching is carried out between the waveform $R(t)$ of the received wave signal and the new waveform $r(t)$ with the round propagation times $T_1$ and $T_2$ varied. In this way, the optimal pattern matching is repeated by adding a new term, until a satisfactory matching angle is obtained. Finally, the defect diagnosis is achieved based on the number of the terms, the signs of the linear combination coefficients, and the round propagation times.

In this example, no sample is required, and a good result can be automatically obtained through calculation. In this case, the linear combination coefficients for the pattern matching are calculated theoretically using the round propagation times, transmittances and a reflectance, and attenuation rate in the concrete structure 11.

Another example is as follows. That is, generally, one of the purposes to carry out the non-destructive inspection of the concrete structure 11 is to detect the defect 15, such as a crack or as cavity, which exists inside the concrete structure 11. Therefore, when carrying out the pattern matching in the non-destructive inspection in such a case, it is enough to consider the following five cases of defects in the depth direction of the concrete structure 11: a case of no defect, a case of one crack, a case of two cracks, a case of one cavity, and a case of one crack and one cavity. In this way, the general pattern matching using the equation (1) is not necessarily needed to be carried out. Instead, the optimal pattern matching is carried out between the received wave signal $R(t)$ and the predicted wave signals generated under the assumptions of the above mentioned five cases (i.e., the five defect hypotheses).

In this example, the waveforms of the predicted wave signals are calculated based on the defect hypotheses and the round propagation times. A pattern matching is carried out between the waveform $R(t)$ of the received wave signal and the waveform of the predicted wave signal under each defect hypothesis by varying the round propagation times, and the least matching angle and the optimal round propagation times are calculated. The minimum matching angle is searched from among the least matching angles. If the minimum matching angle corresponds to either one of the defect hypotheses other than the no-defect hypothesis, it is judged that at least one defect exists in the concrete structure, and the position and size of each cavity or crack can be determined based on the defect hypothesis and the round propagation times $T_1, T_2, T_3, \ldots$, which realize the minimum matching angle. Although the second example would be unlikely to cover every defect, it is practical to use adding that the matching result can be determined faster than in the first example.

When the inner product is calculated in the equation (7), a weighting function may be introduced. By this, since the second term and the subsequent terms are enhanced, the defect detection can be improved, and the position measurement can be achieved in a high reliability.

Also, it is preferable that the optimal pattern matching of the waveform $R(t)$ of a derivative of the received wave signal and the waveform $r(t)$ of the derivative of each of the predicted wave signals is carried out, at the same time as the optimal pattern matching of the waveform $R(t)$ of the received wave signal and the waveform $r(t)$ of each of the predicted wave signals. In this case, the defect detection can be further improved, and the position measurement can be achieved in a high reliability.

Also, in the seeking of the least matching angles for each defect hypothesis, it is preferable to take two steps. That is, in the first step, the least matching angle is roughly calculated, and then in the second step, the least matching angle and the round propagation times realizing it are finely calculated for each defect hypothesis, and finally the minimum matching angler from the least matching angles is sought together with the optimal round propagation times.

Next, the simple method will be described. The above strict method is based on the theoretical consideration. However, the linear combination coefficients do not always meet the above relation. Under the actual situation, the constraint to the linear combination coefficients is loosened and only the constraint on the signs of the linear combination coefficients is implied to the above equation (1). This is referred to as the simple method.

If the optimization is carried out by manipulating both the round propagation times and the linear combination coefficients as variables, there is a risk that the solution falls into one of local solutions located around the true solution. Also, it would take a long time for the calculation. For these reasons, in the simple method, although only the optimization of the round propagation times are carried out numerically, the optimization of the linear combination coefficients is carried out analytically. For this purpose, the waveforms $r_0(t-T_1), r_0(t-T_2), r_0(t-T_3), \ldots, r_0(t-T_k)$ in the equation (1) are represented as $r_1(t), r_2(t), r_3(t), \ldots, r_k(t)$, respectively. Also, the waveform of each fundamental reflected wave signal whose linear combination coefficient is physically negative is treated such that the negative sign is given to the waveform of the corresponding reflected wave signal. Under this procedure, all linear combination coefficients become positive.

Figure 2:
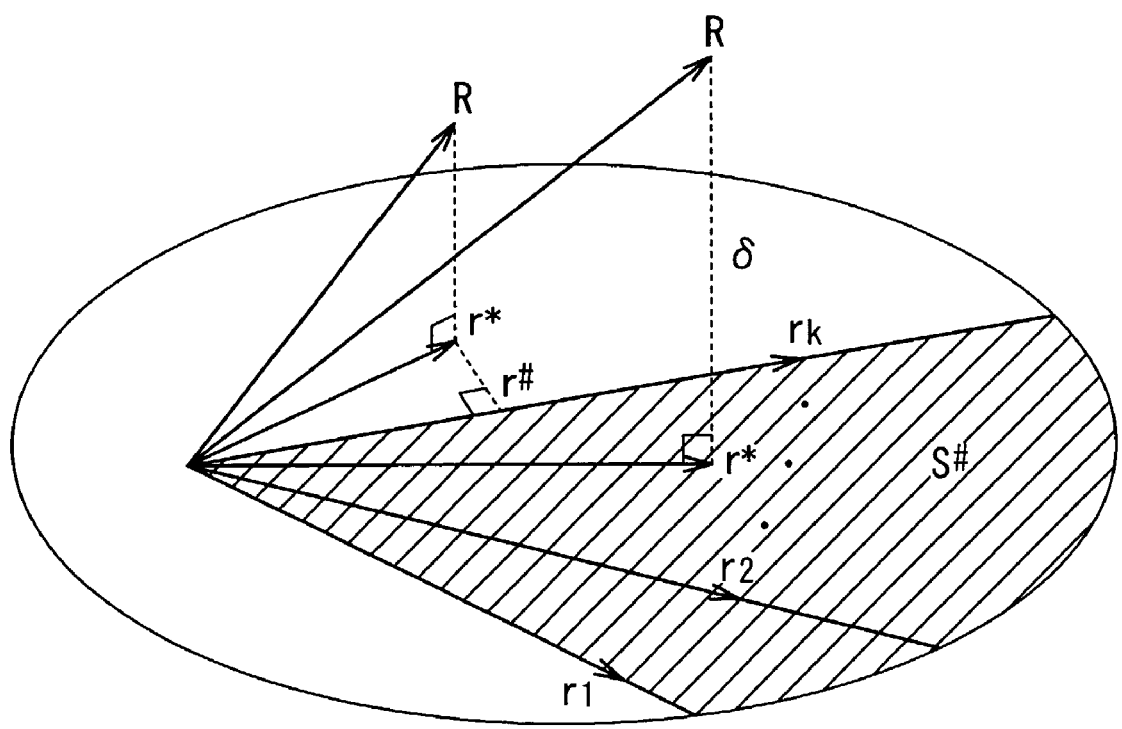
FIG. 2 is a diagram showing an orthogonal projection of a received wave signal for an optimal pattern matching.

At first, for each defect hypothesis, the optimal linear combination coefficients $c_1, c_2, c_3, \ldots, c_k$ (all of them are positive) to attain the optimal pattern matching are calculated as functions of the corresponding round propagation times $T_1, T_2, T_3, \ldots, T_k$. Here, the waveform $R(t)$ of the actual received wave signal is orthogonally projected into a space which is spanned by the waveforms $r_j(t)$ ($1 \leq j \leq k$) defined above. A hatching region shows the space spanned by the waveforms $r_j(t)$ ($1 \leq j \leq k$) under the positive linear combinations as shown in FIG. 2. In this case, it is known that the orthogonally projected point $r^*$ is the optimal solution if the point $r^*$ is contained in the hatching region $S^{\#}$. An optimal approximation error $\delta$ at this time is represented by the following equation (8).

$$\delta = \sqrt{\frac{g(r_1, r_2, \ldots, r_k, R)}{g(r_1, r_2, \ldots, r_k)}} \qquad (8)$$

where $g(r_1, r_2, r_3, \ldots, r_k)$ is a Gramian with the arguments as its components. Thus, the optimal matching angle $\theta$ is given by the following equation (9).

$$\theta = \sin^{-1}[\delta/\|R\|] \qquad (9)$$

where $\|R\|$ is a norm of R. Also, at the same time, the linear combination coefficients $c_1, c_2, c_3, \ldots, c_k$ are obtained analytically from the following equation (10).

$$r^* = -\frac{\begin{vmatrix} (r_1, r_1) & (r_1, r_2) & \cdots & (r_1, r_k) & r_1 \\ (r_2, r_1) & (r_2, r_2) & \cdots & (r_2, r_k) & r_2 \\ \vdots & \vdots & \ddots & \vdots & \vdots \\ (r_k, r_1) & (r_k, r_2) & \cdots & (r_k, r_k) & r_k \\ (R, r_1) & (R, r_2) & \cdots & (R, r_k) & 0 \end{vmatrix}}{g(r_1, r_2, \ldots, r_k)} \qquad (10)$$

$$= c_1^* r_1 + c_2^* r_2 + \ldots c_k^* r_k$$

If the linear combination coefficients $c_1^*, c_2^*, c_3^*, \ldots, c_k^*$ thus analytically obtained are all positive, the orthogonally projected wave signal $r^*$ given by the equation (10) is the optimal pattern matching solution. The angle $\theta$ of the equation (9) becomes the optimal matching angle which provides the similarity of the waveform $r^*$ of the orthogonally projected wave signal to the waveform $R(t)$ of the actual received wave signal.

On the other hand, if a part of the linear combination coefficients $c_1^*, c_2^*, c_3^*, \ldots, c_k^*$ is negative, the orthogonally projected point $r^*$ is located at a point outside the hatching region $S^\#$ and is not the optimal solution calculated under the constraint on the signs of the linear combination coefficients. In this case, another point $r^\#$ is calculated which is the closest to the boundary surface of the convex cone region $S^\#$. The calculated point $r^\#$ is the waveform closest to the waveform $R(t)$ of the actual received wave signal under the constraint.

Thus, the optimal matching angle $\theta$ in the case is calculated by the following equation (11).

$$\theta = \cos^{-1}\left[\frac{(R, r^\#)}{\|R\| \cdot \|r^\#\|}\right] \qquad (11)$$

It should be noted that the waveform $r^\#$ is calculated by the orthogonal projection of $r^*$ to the space spanned by several waveforms $r_j(t)$ whose linear combination coefficients calculated from the equation (10) are positive.

In this way, in the pattern matching section 22, the optimal linear combination coefficients $c1^*, c_2^*, c_3^*, \ldots, c_k^*$ and an optimal matching angle $\theta$ are determined for each of the five cases: the case of no defect, the case of one crack, the case of two cracks, the case of one cavity, and the case of one crack and one cavity, in the depth direction of the concrete structure 11.

Subsequently, the angle $\theta$ is minimized with respect to the round propagation times $T_1, T_2, T_3, \ldots, T_k$ to evaluate the probability of each hypothesis to be true based on the least matching angle. Therefore, the defects inside the concrete structure 11 are determined based on the defect hypothesis which minimizes the least matching angle $\propto^*$. Moreover, the positions of the respective defects 15 are determined using the optimal round propagation times $T_1, T_2, T_3, \ldots, T_k$ of the selected defect hypothesis. Together with the form of the defect, the data of the specific positions of the respective defects 15 is finally represented on the display 24 and outputted from the printer 25 by the output processing section 26.

In the above strict method, the linear combination coefficients of the predicted wave signal are calculated theoretically. However, the round propagation times must be assigned. In this case, the waveform synthesizing section 21 makes the waveform $r(t)$ of the predicted wave signal in the form of the equation (1) while varying the round propagation times $T_1, T_2, T_3, \ldots$ under each defect hypothesis. Thus, the pattern matching section 22 makes the optimal predicted wave signal with the defect hypothesis and the round propagation times optimally adjusted.

Also, in the simple method, for each defect hypothesis, the pattern matching section 22 determines the optimal linear combination coefficients $C_1, c_2, \ldots$ analytically for given round propagation times and then calculates the optimal matching angle between the waveform $R(t)$ of the received wave signal and the waveform $r(t)$ of the optimal predicted wave signal for each defect hypothesis by varying the round propagation times. Subsequently, the pattern matching section 22 selects the defect hypothesis which takes the minimum matching angle over the optimal matching angles. The pattern matching section 22 determines the positions of the defects based on the optimal round propagation times $T_1, T_2, \ldots$ for the selected defect hypothesis.

Next, the first experiment to obtain the fundamental reflected wave will be described.

The transmitting and receiving antennas were set on the surface of a concrete structure with a little distance (e.g., 10 mm) from the concrete surface. In this case, the thickness of the concrete structure was 500 mm, and thus the reflected wave signal from only the concrete surface could be independently obtained. FIG. 3 shows the waveform of a received wave signal obtained by the receiving antenna at this time. It should be noted that when the electromagnetic wave signal is reflected from the concrete surface, its phase is shifted by 180 degrees. Thus, the waveform of the received wave signal received by the receiving antenna was inversed in sign like a waveform indicated by a dotted curve in FIG. 3, and this can be used as the fundamental reflected wave. When the positions of a crack and the like are determined, a propagation velocity v of the electromagnetic wave signal is used. It is represented by $v=s/\in^{1/2}$ where a relative dielectric constant of the concrete structure as a propagation medium is represented by $\in$ ($\in$ is a velocity of a light). Hence, the propagation velocities in the air and the concrete are assumed to be $3.0 \times 10^8$ m/sec and $1.1 \times 10^8$ m/sec, respectively, since the relative dielectric constants of the air and the concrete are 1 and 8, respectively.

Next, the detection operation in an experiment will be described.

Figure 4:
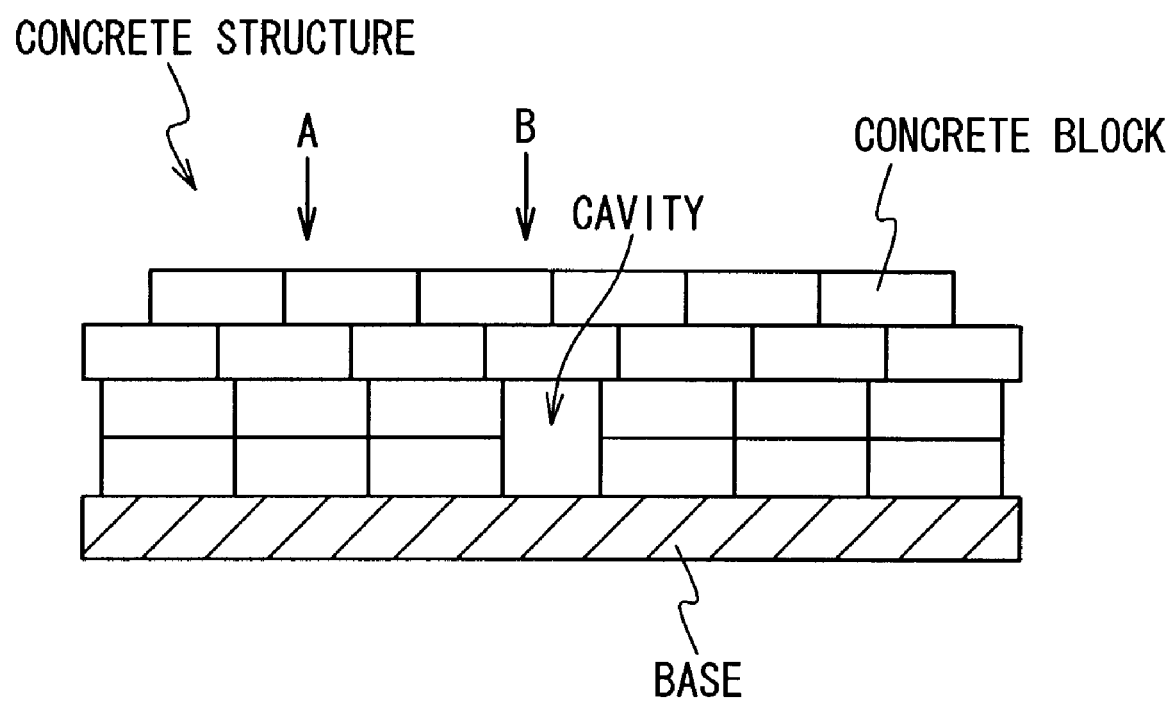
FIG. 4 is a diagram showing a concrete structure to be non-destructively inspected.

Concrete blocks were produced to have the thickness of 60 mm and lateral and longitudinal widths of 300 mm, respectively, and four layers thereof were piled up on a base, as shown in FIG. 4. This was intended to produce the situations that a plurality of cracks existed in depth direction and that a cavity and a crack coexisted.

Figure 5:
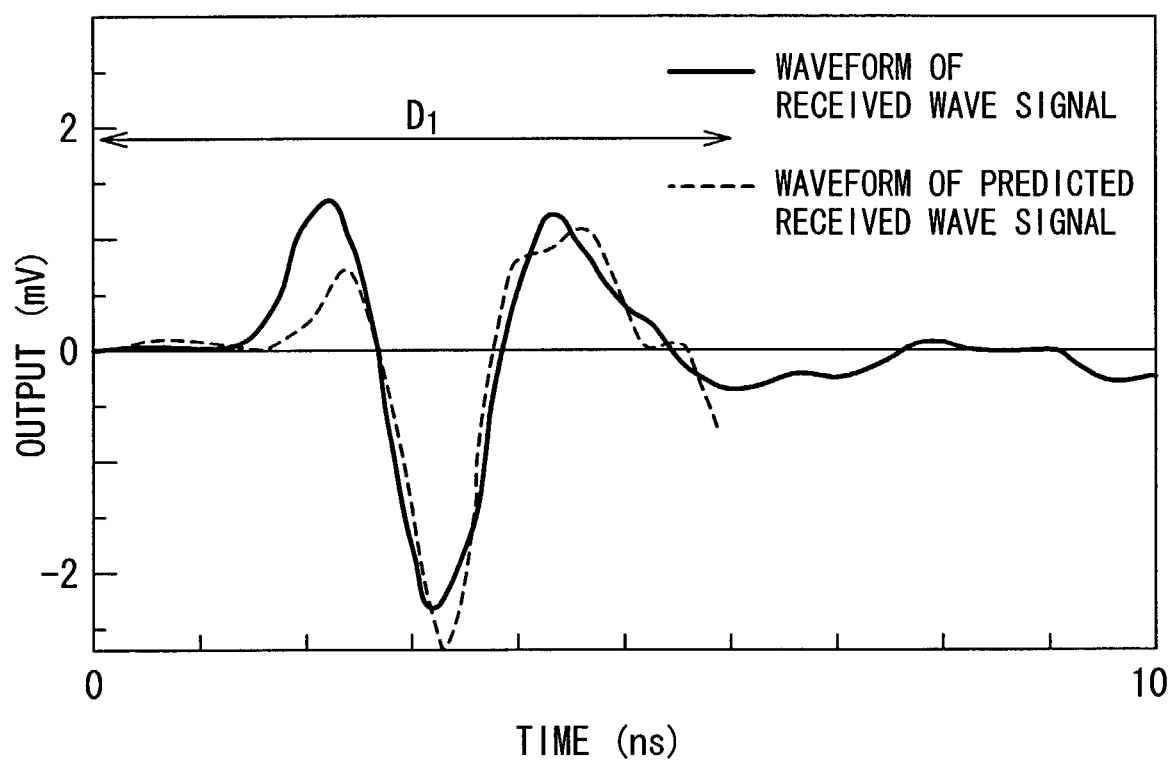
FIG. 5 is a graph showing the similarity between the waveform of an optimal predicted wave signal and the waveform of a received wave signal.
Figure 6:
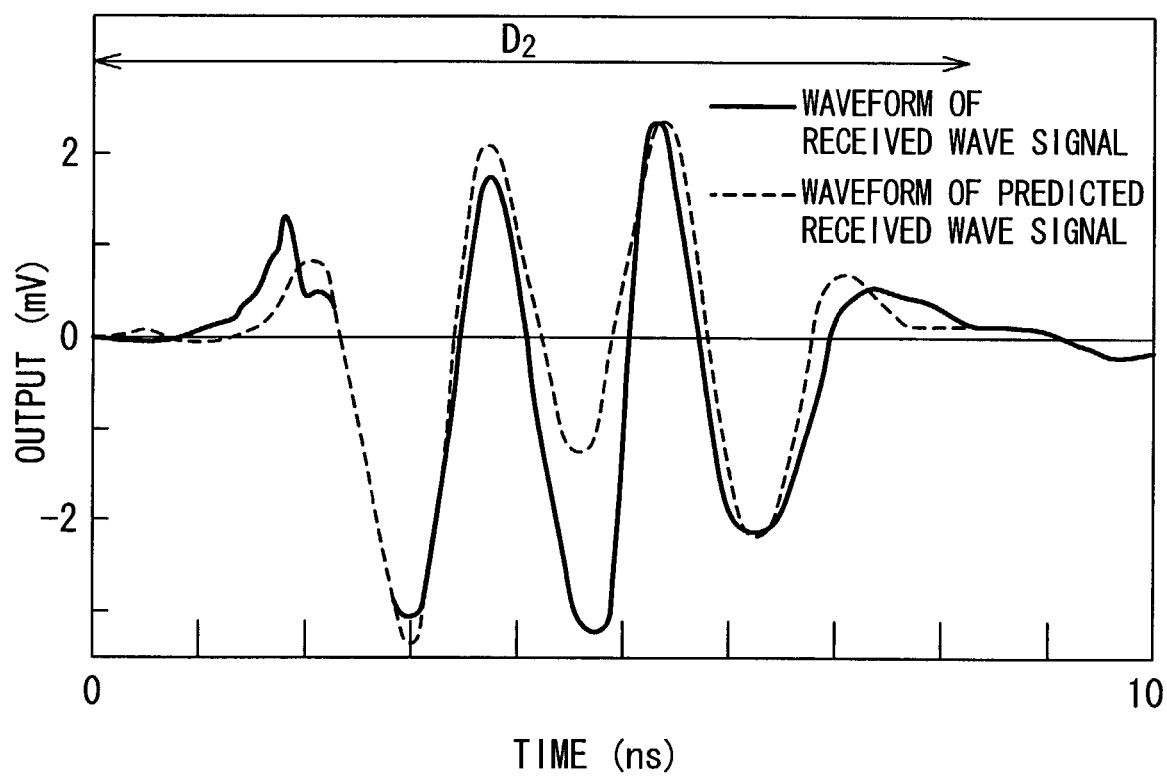
FIG. 6 is another graph showing the similarity between the waveform of an optimal predicted wave signal and the waveform of a received wave signal.

At first, in order to examine the effectiveness of the detection of the crack, the transmitting and receiving antennas were located at a point A of FIG. 4 with the distance 10 mm from the concrete surface. FIG. 5 shows the waveform of the received wave signal from the concrete structure at this time.

It should be noted that the pattern matching was performed on the cases of the five kinds of defects, such as (1) case of no defect, (2) case of one crack, (3) case of two cracks, (4) case of one cavity, and (5) case of one crack and one cavity, respectively, with the data window D1 of the interval 0 to 6 ns, on which a meaningful signal was observed in FIG. 5. The Table 1 shows the measurement results of the optimal matching angles and the positions of the crack and the cavity for each defect hypothesis for the above simple method.

TABLE 1

| | Kind of Defect | Optimal Matching Angle (°) | Measurement Depth (mm) |
|---|---|---|---|
| 1 | No Defect | 29.4 | |
| 2 | One Crack | 22.5 | 81.0 |
| 3 | Two Cracks | 19.0 | 77.5, 118.0 |
| 4 | One Cavity | 19.9 | 81.0, 255.0 |
| 5 | One Crack and One Cavity | 18.9 | 72.0, 108.0, 337.0 |
| 6 | Three Cracks | 18.3 | 72.0, 117.0, 171.0 |

Table 1 also shows the measurement result in a case of three cracks in order to see how many cracks are detectable with the method. The linear combination coefficients for the respective cases are shown, for reference, as follows. (1) −1.13, (2) −1.12, 0.38, (3) −1.07, 0.61, 0.39, (4) −1.11, 0.43, −1.00, (5) −1.05, 0.55, 0.38, −0.61, and (6) −1.03, 0.73, 0.97, 2.03. The values with negative sign represent that the phase of the reflected wave signals are opposite to that of the fundamental reflected wave.

From the Table 1, at the sixth case where three cracks are assumed inside the concrete structure, the optimal matching angle has the minimum value of 18.3 degrees. It could be understood that the waveform of the optimal predicted wave signal for the sixth hypothesis is the closest to the waveform of the actual received wave signal. The dotted curve in FIG. 5 shows the waveform of the optimal predicted wave signal at the time. Thus, the defects inside the concrete structure can be determined as the sixth case, that is three cracks. At this time, the measured results of the crack positions are 72.0 mm, 117.0 mm and 171.0 mm, respectively. The values are considerably close to the actual values of 60 mm, 120 mm and 180 mm. Hence, confirmed is the effectiveness of the non-destructive inspection method of this concrete structure.

Also, in the fifth case where the optimal matching angle is the second smallest, the first two round propagation times are substantially equal to those of the sixth case (i.e., the case of three cracks). However, the propagation velocity in the cavity is faster by about three times than that in the concrete. Thus, the result shows that the crack and the upper surface of the cavity are located at almost the same positions as the upper two cracks, whereas the bottom surface of the cavity goes down to the depth of 337.0 mm. Also, even in the third case where the optimal matching angle is the third smallest, namely, in the case where the number of cracks is assumed to be 2, it is understood that the two crack positions are substantially exactly measured.

Next, another experimental result will be described. The case of the co-existence of a crack and a cavity in depth direction was examined. The transmitting and receiving antennas were located at a point B of FIG. 4 with the distance of 10 mm from the front surface of the concrete structure, and the experiment was carried out. This experiment implies the situation that a crack exists at the position of 60 mm deep from the front surface of the concrete structure and a cavity of the thickness of 120 mm exists at the position of 120 mm from the front surface.

It should be noted that in the pattern matching, the data window D2 of the interval of 0 to 8.5 ns is used, because a meaningful signal is observed in the interval. For this data, the optimal matching angles and the positions of the defects were determined by the above mentioned simple method under the cases of the following six kinds of defect: (1) case of no defect, (2) case of one crack, (3) case of two cracks, (4) case of one cavity, (5) case of one crack and one cavity, and (6) case of three cracks. The following table 2 shows the measurement results. In this case, the linear combination coefficients are as follows. (1) −1.46, (2) −1.48, 1.43, (3) −1.28, 0.39, 1.40, (4) −1.30, 1.28, −2.71, (5) −1.20, 0.49, 1.12, −0.58, and (6) −1.27, 0.39, 1.39, 0.19.

TABLE 2

| | Kind of Defect | Optimal Matching Angle (°) | Measurement Depth (mm) |
|---|---|---|---|
| 1 | No Defect | 48.1 | |
| 2 | One Crack | 33.1 | 135.0 |
| 3 | Two Cracks | 31.8 | 49.5, 135.0 |
| 4 | One Cavity | 30.0 | 76.5, 89.2 |
| 5 | One Crack and One Cavity | 28.9 | 49.5, 135.0, 262.0 |
| 6 | Three Cracks | 31.4 | 49.5, 135.0, 229.5 |

From the table 2, in the fifth case where one crack and one cavity are assumed to exist inside the concrete, the optimal matching angle between the waveform of the received wave signal and the waveform of the optimal predicted wave signal has a minimum value of 28.9 degrees. It could be understood that the waveform of the actual received wave signal is the most exactly represented by the waveform of the optimal predicted wave signal under the defect hypothesis (i.e., the fifth case). Thus, the defect inside the concrete structure can be determined as the fifth case, namely, the case where there is one crack and one cavity. At this time, the positions of the crack, the upper surface of the cavity and the bottom surface of the cavity are respectively 49.5 mm, 135.0 mm and 262.0 mm from the surface. The values are all close to the actually measured values of 60 mm, 120 mm and 240 mm. Hence, confirmed is the effectiveness of the non-destructive inspection method of concrete structure. Although only the effectiveness of the simple method is confirmed above, the effectiveness of the strict method is similarly confirmed, though it is omitted here.

To non-destructive inspections of non-concrete structures, the present invention can be similarly applied by replacing "the concrete structure" by "a non-concrete structure" and replacing "the non-concrete body existing inside the concrete structure" by "a foreign substance whose property is different from a non-concrete structure existing inside a non-concrete structure", respectively. Thus, the description of a non-destructive inspection apparatus according to the second embodiment of the present invention is omitted.

It should be noted that it is possible to consider a mixture as the non-concrete structure in which slug floats on melted iron. By applying the non-destructive inspection method of the non-concrete structure to this mixture of the slug and the melted iron, it is possible to measure the thickness of the slug and the position of the melted iron.

The present invention have been described. However, the present invention is not limited to those embodiments. For example, it can be applied not only to the detection of the cracks and cavities inside the concrete structure and the measurement of those positions, but as so the measurement of the coverage of concrete over a reinforcing bar, namely, a distance between the concrete surface and the reinforcing bar and the like. It should be, however, noted that a relative dielectric constant in the concrete is not exactly known, although it is within a certain range. Thus, in order to accurately measure the coverage of the concrete over the reinforcing bars, it is necessary to measure this relative dielectric constant, too. For this purpose, in addition to the position data of the transmitting and receiving antennas of the electromagnetic wave radar, a position, a two-dimensional direction and a diameter of the reinforcing bar, and a relative dielectric constant in the concrete must be treated as parameters, and Snell's law is applied to them in a good manner. Then, the propagation time of the electromagnetic wave is theoretically predicted using these parameters. Then, the parameters' adjustment (or optimization) is carried out so that the actually measured propagation time coincides with the time predicted by the above-mentioned theoretical method. Consequently, it is possible to accurately measure not only the coverage, but also the interval between the reinforcing bars, the position thereof (including the depth and the direction), the diameter and the like. In this case, it is possible that the electromagnetic wave signal is not vertically incident to the concrete surface and the reinforcing bars. In the case, Snell's law had better be applied to the above-proposed method.

Also, the signal of the fundamental reflected wave signal can be made larger and sharper by generating a series of impulses on the electromagnetic wave radar instead of one isolated impulse. Thus, it is possible to make the detection depth deeper. Or, even if a distance between a plurality of cracks is short, it is possible to further accurately identify and detect them.

Moreover, the linear combination of the fundamental reflected waveforms is employed in the optimal pattern matching between the waveform of the actually received wave signal and the waveform of the predicted wave signal. However, as the propagation distance in the concrete is longer, the attenuation of the high frequency component is larger, which usually leads to the change in the propagation waveform. Hence, in view of this change, if the fundamental reflected waveform whose shape is slightly changed on the basis of the depth of the crack and the cavity is determined theoretically and/or experimentally and the pattern matching is carried out under the linear combination of them, it is possible to establish the non-destructive inspection method of the concrete structure having a higher accuracy.

It should be noted that when the non-destructive inspection is carried out, the first order reflected wave from the concrete surface is always received. Thus, in the actual non-destructive inspection, if the first order reflected wave signal from the concrete surface is stored and the above-mentioned methods (i.e., the strict and simple methods) are applied to a signal in which the first order reflected wave signal may be subtracted from the actual received wave signal, the number of fundamental reflected waves linearly combined can be reduced by 1. Moreover, the first order reflected wave signal from the concrete surface is considered to be slightly different in shape from the reflected waves from the non-destructive target inside the concrete structure. Hence, a slight change in the reflected waves may be effective in improving the measurement accuracy of the proposed system.

As described above, according to the non-destructive inspection method of the present invention, the non-concrete body is detected by applying the above-mentioned strict method or simple method to the concrete structure. The non-destructive inspection method of the present invention can be applied to a non-concrete structure in addition to the concrete structure. When the non-destructive inspection method of the present invention can be applied to a non-concrete structure, different substance structures, such as a steel skeleton, a reinforcing bar, a foreign substance inside the non-concrete structure can be accurately detected, and the position can be also measured in a short time with a high accuracy.

In particular, in the non-destructive inspection method of the present invention, the waveform of each of the predicted wave signals is represented as a linear combination of the waveforms of the fundamental reflected wave signals with the round propagation times as variables for the defect hypotheses. By carrying out the optimal pattern matching between the waveform of the received wave signal and the waveform of each of the predicted wave signals while the round propagation times are varied, the optimal defect hypothesis is found from the least matching angles. The kinds and number of defects are determined from the optimal defect hypothesis and the positions of the defects are determined from the round propagation times.

What is claimed is:

1. A non-destructive inspection apparatus comprising:
    a transmission section operable to irradiate a pulse-actuated electromagnetic wave wirelessly through an inspection target;
    a reception section operable to receive a reflected electromagnetic wave from the inspection target to generate a received wave signal; and
    a processing unit operable to generate a fundamental wave signal for a fundamental reflected electromagnetic wave predicted to be received from each of a number of reflection points of the inspection target theoretically or experimentally based on the received wave signal from a reflection point of a reference target or each of a number of reflection points of a plurality of reference targets, and determine existence or nonexistence of at least one defect in the inspection target based on a waveform of the received wave signal and a waveform of the fundamental wave signal.

2. The non-destructive inspection apparatus according to claim 1, wherein said processing unit carries out a pattern matching between the waveform of the received wave signal and the waveform of the fundamental wave signal and determines the existence or nonexistence of said at least one defect in the inspection target based on the pattern matching result.

3. A non-destructive inspection apparatus comprising:
    a transmission section operable to irradiate an electromagnetic wave signal toward an inspection target;
    a reception section operable to receive a reflected electromagnetic wave signal from said inspection target to generate a received wave signal; and
    a processing unit operable to generate a fundamental wave signal for a fundamental reflected electromagnetic wave signal predicted to be received from each of a number of reflection points of the inspection target, and determine existence or nonexistence of at least one defect in the inspection target based on the received wave signal and said fundamental wave signal,
    wherein said processing unit generates predicted wave signals under defect hypotheses, when said at least one defect is determined to exist, each of the predicted wave signals being a linear combination of said fundamental wave signals with different round propagation times relating to said at least one defect as variables, and
    wherein said processing unit carries out a pattern matching between a waveform of the received wave signal and a waveform of each of said predicted wave signals and determines said at least one defect in the inspection target based on the pattern matching result.

4. The non-destructive inspection apparatus according to claim 3, wherein said processing unit comprises:
- a waveform synthesizing section operable to generate said predicted wave signals under said defect hypotheses in which defects are different in number and types, when it is determined that said at least one defect exists in the inspection target; and
- a pattern matching section operable to carry out said pattern matching between the waveform of the received wave signal and the waveform of each of the predicted wave signals to determine a least matching angle under each of the defect hypotheses, determine a minimum matching angle from among the least matching angles for the defect hypotheses, and determine one of the defect hypotheses realizing the minimum matching angle.

5. The non-destructive inspection apparatus according to claim 4, wherein the defect hypotheses are a case of one crack, a case of two cracks, a case of one cavity, and a case of one crack and one cavity.

6. The non-destructive inspection apparatus according to claim 4, wherein said pattern matching section determines a number of said at least one defect, a type of each of said at least one defect, and a position of each of said at least one defect based on the predicted wave signals calculated for the determined defect hypothesis.

7. The non-destructive inspection apparatus according to claim 4, wherein
said pattern matching section determines the least matching angle between the waveform of the received wave signal and the waveform of a corresponding one of the predicted wave signals for every defect hypothesis while varying the round propagation times.

8. The non-destructive inspection apparatus according to claim 4, wherein said pattern matching section determines an optimal approximation error when the received wave signal is orthogonally projected to a space spanned by the fundamental wave signals corresponding to each of the defect hypotheses under constraint of a sign on each of linear combination coefficients while varying the round propagation times of the fundamental wave signals, and determines the least matching angle for each defect hypothesis based on the optimal approximation error and the received wave signal.

9. The non-destructive inspection apparatus according to claim 4, wherein said pattern matching section determines an optimal predicted wave signal such that a difference between the received wave signal and the predicted wave signal from the fundamental wave signals corresponding to each of the defect hypotheses is minimized, varying the round propagation times of the fundamental wave signals, and determines the least matching angle for each of the defect hypotheses based on the optimal predicted wave signal and the received wave signal.

10. The non-destructive inspection apparatus according to claim 4, wherein said pattern matching section introduces a weight on at least one part of the waveform of the received wave signal to decrease an effect from the received wave signal from a surface of the inspection target.

11. The non-destructive inspection apparatus according to claim 4, wherein said pattern matching section generates derivatives of the received wave signal and each of the predicted wave signals and carries out the pattern matching between the derivatives corresponding to the received wave signal and each of the predicted wave signals.

12. The non-destructive inspection apparatus according to claim 3, wherein linear combination coefficients of the linear combination of said fundamental wave signals and different round propagation times are determined based on each of the defect hypotheses.

13. A non-destructive inspection method comprising:
- irradiating a pulse-actuated electromagnetic wave toward an inspection target;
- receiving a reflected electromagnetic wave from the inspection target to generate a received wave signal;
- providing a fundamental wave signal for a fundamental reflected wave signal predicted to be received from each of a number of reflection points of the inspection target theoretically or experimentally based on the received wave signal from a reflection point of a reference target or each of a number of reflection points of a plurality of reference targets;
- determining existence or nonexistence of said at least one defect in the inspection target based on a waveform of the received wave signal and a waveform of the fundamental wave signal;
- when said at least one defect is determined to exist, generating predicted wave signals which are closer to the received wave signal under several defect hypotheses; and
- determining a number of said at least one defect, a type of each of said at least one defect, and a position of each of said at least one defect in the inspection target based on the closest waveform of the predicted wave signals.

14. The non-destructive inspection method according to claim 13, wherein the defect hypotheses are a case of one crack, a case of two cracks, a case of one cavity, and a case of one crack and one cavity.

15. A non-destructive inspection method comprising:
- irradiating an electromagnetic wave signal toward an inspection target;
- receiving a reflected electromagnetic wave signal from said inspection target to generate a received wave signal;
- providing a fundamental wave signal for a fundamental reflected electromagnetic wave signal predicted to be received from each of a number of reflection points of the inspection target theoretically or experimentally based on the received wave signal from a reflection point of a reference target or each of a number of reflection points of reference targets;
- determining existence or nonexistence of at least one defect in said inspection target based on a waveform of the received wave signal and a waveform of said fundamental wave signal;
- when said at least one defect is determined to exist, generating predicted wave signals based on defect hypotheses;
- determining a number of said at least one defect, a type of said at least one defect, and a position of said at least one defect in said inspection target based on the waveform of the received wave signal and a waveform of each of the predicted wave signals,
- wherein each of the predicted wave signals is a linear combination of fundamental wave signals with round propagation times relating to said at least one defect as variables.

16. The non-destructive inspection method according to claim 15, wherein said determining of the existence or nonexistence of said at least one defect comprises:
- carrying out a pattern matching between the waveform of the received wave signal and the waveform of the fundamental wave signal; and determining the existence or nonexistence of said at least one defect in the inspection target based on the pattern matching result.

17. The non-destructive inspection method according to claim 15, wherein said determining of the number of said at least one defect, the type of each of said at least one defect, and the position of each of said at least one defect comprises:
   determining a least matching angle for each of the defect hypotheses based on the waveform of the received wave signal and the waveform of a corresponding one of the predicted wave signals.

18. The non-destructive inspection method according to claim 17, wherein said determining of the least matching angle comprises:
   carrying out a pattern matching between the waveform of the received wave signal and the waveform of each of the predicted wave signals to determine the least matching angle for a corresponding one of the defect hypotheses.

19. The non-destructive inspection method according to claim 15, wherein said determining of the number of said at least one defect, the type of each of said at least one defect, and the position of each of said at least one defect further comprises:
   determining a minimum matching angle from among least matching angles for the defect hypotheses; and
   determining one of the defect hypotheses corresponding to the minimum matching angle.

20. The non-destructive inspection method according to claim 19, wherein said determining of the number of said at least one defect, the type of each of said at least one defect, and the position of each of said at least one defect further comprises:
   determining the number of said at least one defect and the type of each of said at least one defect based on the determined defect hypothesis; and
   determining the position of each of said at least one defect based on round propagation times relating to the determined defect hypothesis.

21. The non-destructive inspection method according to claim 15, wherein said determining of the number of said at least one defect, the type of each of said at least one defect, and the position of each of said at least one defect comprises:
   determining an optimal approximation error when the received wave signal is orthogonally projected to a space spanned by the fundamental wave signals defined by each of the defect hypotheses under constraint of a sign of each of linear combination coefficients while varying the round propagation times of the fundamental wave signals; and
   determining a least matching angle for each of the defect hypotheses based on the optimal approximation error and the received wave signal.

22. The non-destructive inspection method according to claim 15, wherein said determining of the number of said at least one defect, the type of each of said at least one defect, and the position of each of said at least one defect comprises:
   determining an optimal predicted wave signal such that a difference between the received wave signal and a corresponding one of the predicted wave signals from the fundamental wave signals corresponding to each of the defect hypotheses is minimized, varying the round propagation times of the fundamental wave signals; and
   determining the least matching angle for each of the defect hypotheses based on the optimal predicted wave signal and the received wave signal.

* * * * *